United States Patent
Hendriks et al.

(10) Patent No.: US 9,840,109 B2
(45) Date of Patent: Dec. 12, 2017

(54) ENGINEERED SURFACE FOR PROVIDING LOW FRICTION AND IMPROVED COMFORT ON DEVICES THAT CONTACT THE SKIN OR OTHER EXTERNAL TISSUE OF THE USER

(71) Applicant: KONINKLIJKE PHILIPS N.V., Eindhoven (NL)

(72) Inventors: Cornelis Petrus Hendriks, Eindhoven (NL); Rudolf Maria Jozef Voncken, Eindhoven (NL); Willem Potze, Geldrop (NL); Nicolaas Petrus Willard, Valkenswaard (NL); Joyce Van Zanten, Waalre (NL); Mareike Klee, Straelen (DE)

(73) Assignee: Koninklijke Philips N.V., Eindhoven (NL)

( * ) Notice: Subject to any disclaimer, the term of this patent is extended or adjusted under 35 U.S.C. 154(b) by 298 days.

(21) Appl. No.: 14/370,987

(22) PCT Filed: Jan. 9, 2013

(86) PCT No.: PCT/IB2013/050190
§ 371 (c)(1),
(2) Date: Jul. 8, 2014

(87) PCT Pub. No.: WO2013/108154
PCT Pub. Date: Jul. 25, 2013

(65) Prior Publication Data
US 2014/0349075 A1  Nov. 27, 2014

Related U.S. Application Data

(60) Provisional application No. 61/586,865, filed on Jan. 16, 2012.

(51) Int. Cl.
*B44F 9/00* (2006.01)
*H04R 1/10* (2006.01)
(Continued)

(52) U.S. Cl.
CPC .............. *B44F 9/00* (2013.01); *A61B 5/681* (2013.01); *A61J 9/00* (2013.01); *B29C 37/0053* (2013.01);
(Continued)

(58) Field of Classification Search
CPC ..... Y10T 428/24479; Y10T 428/24612; B32B 3/30; H04R 1/10; H04R 1/12; A61M 1/06;
(Continued)

(56) References Cited

U.S. PATENT DOCUMENTS 5,753,343 A    5/1998   Braun et al.
6,372,323 B1   4/2002   Kobe et al.
(Continued)

FOREIGN PATENT DOCUMENTS

EP   1652545 A1   5/2006
EP   1707234 A1   10/2006
(Continued)

OTHER PUBLICATIONS

Translation of EP1652545.*

*Primary Examiner* — Catherine A Simone (57) ABSTRACT

An apparatus structured to contact external tissue, such as skin, of a user includes an elastomeric contacting portion that is structured to directly engage the external tissue. The contacting portion has an engineered surface (64A, 64B) that includes a plurality of non-random, predesigned surface features (70, 74B, 76B, 78B) designed to reduce friction and improve user comfort. In one implementation, the pitch (P) between each immediately adjacent pair of the surface
(Continued)

features (70, 76B) is less than or equal to a predetermined maximum pitch value, and the height (H) of each of the surface features (70, 76B) is less than or equal to a predetermined maximum height value.

11 Claims, 11 Drawing Sheets (51) Int. Cl.
| | | |
|---|---|---|
| *B44C 1/00* | (2006.01) | |
| *A61J 9/00* | (2006.01) | |
| *A61M 1/06* | (2006.01) | |
| *A61B 5/00* | (2006.01) | |
| *B29C 37/00* | (2006.01) | |
| *H04R 1/12* | (2006.01) | |

(52) U.S. Cl.
CPC ............... *B44C 1/005* (2013.01); *H04R 1/10* (2013.01); *A61M 1/066* (2014.02); *H04R 1/12* (2013.01); *Y10T 428/24479* (2015.01)

(58) Field of Classification Search
CPC .. A61M 1/066; A61J 9/00; A61J 13/00; A61J 9/0623; A61J 9/06; A61J 17/00; A61J 17/02; A61J 17/008; A61J 17/001; A61J 11/00; A61J 11/0035; A61J 11/005; A61J 11/0045; A61J 11/0055; A61B 5/681; B44C 1/005
See application file for complete search history.

(56) References Cited

U.S. PATENT DOCUMENTS

| | | | |
|---|---|---|---|
| 6,461,324 | B1 | 10/2002 | Schlensog |
| 7,522,743 | B2 | 4/2009 | Dobras et al. |
| 9,456,961 | B2 | 10/2016 | Duineveld |
| 2002/0020688 | A1 | 2/2002 | Sherman et al. |
| 2002/0026943 | A1 | 3/2002 | Castiglione |
| 2009/0107515 | A1 | 4/2009 | Gavriely |
| 2010/0018534 | A1 | 1/2010 | Veliss et al. |
| 2010/0065059 | A1 | 3/2010 | Ho |
| 2011/0023882 | A1 | 2/2011 | Nickol et al. |
| 2011/0088699 | A1 | 4/2011 | Skipper et al. |
| 2011/0146684 | A1 | 6/2011 | Wells et al. |
| 2012/0202009 | A1 * | 8/2012 | Motofuji ............. B29C 33/3857 428/156 |

FOREIGN PATENT DOCUMENTS

| | | | |
|---|---|---|---|
| EP | 2281595 A1 | 2/2011 | |
| WO | 2009026627 A1 | 3/2009 | |
| WO | WO 2009093173 A1 * | 7/2009 | ............ A61J 11/005 |
| WO | 2010139014 A1 | 12/2010 | |
| WO | WO 2011048988 A1 * | 4/2011 | ......... B29C 33/3857 |
| WO | 2011/138735 | 11/2011 | |

* cited by examiner

ENGINEERED SURFACE FOR PROVIDING LOW FRICTION AND IMPROVED COMFORT ON DEVICES THAT CONTACT THE SKIN OR OTHER EXTERNAL TISSUE OF THE USER

CROSS REFERENCE TO RELATED APPLICATIONS

This application is a national filing of PCT application Serial No. PCT/IB2013/050190, filed. Jan. 9, 2013, published as WO 2013/105154 A1 on Jul. 25, 2013, which claims the benefit of U.S. provisional application Ser. No. 61/586,855 filed Jan. 16, 2012, which is incorporated herein by reference.

BACKGROUND OF THE INVENTION

1. Field of the Invention

The present invention pertains to devices that have a surface that is structured to contact the skin or other external tissue (e.g., lips) of the user.

2. Description of the Related Art

A variety of devices is known that, during use, come into contact with skin. Examples of such devices are, without limitation, earphones, dust masks, baby bottles, and breast pumps. Use of such devices, especially prolonged use, may cause skin irritation or other kinds of discomfort.

Thus, there is a need for a surface for use in a device, such as earphones, a baby bottle, or a breast pump, that is structured to contact the skin or other external tissue of the user for prolonged periods that provides reduced friction and/or increased comfort for the user.

SUMMARY OF THE INVENTION

Accordingly, it is an object of the present invention to provide an apparatus that has a surface that is structured to contact the skin or other external tissue (e.g., lips) of the user that overcomes the shortcomings of conventional devices by providing reduced friction and/or improved user comfort.

It is yet another object of the present invention to provide a method of making an apparatus that has a surface that is structured to contact the skin or other external tissue (e.g., lips) that does not suffer from the disadvantages associated with conventional design and manufacturing techniques.

In one embodiment, an apparatus structured to contact external tissue, such as skin or the lips, of a user during use thereof is provided. The apparatus includes a contacting portion structured to directly engage the external tissue. At least a section contacting portion has an engineered surface including a plurality of non-random, predesigned surface features each having a similar geometry, wherein in the section the pitch between each immediately adjacent pair of the surface features is less than or equal to a predetermined maximum pitch value, and wherein in the section the height of each of the surface features is less than or equal to a predetermined maximum height value.

In another embodiment, a method of making an apparatus structured to contact external tissue of a user during use thereof is provided. The method includes designing an engineered surface wherein at least a section of the engineered surface comprises a plurality of non-random, predesigned surface features each having a similar geometry, wherein in the section a pitch between each immediately adjacent pair of the surface features is less than or equal to a predetermined maximum pitch value, and wherein in the section a height of each of the surface features is less than or equal to a predetermined maximum height value, and forming a contacting portion for the apparatus in a manner wherein the contacting portion includes the engineered surface, the contacting portion being structured to directly engage the external tissue of the user.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1A:
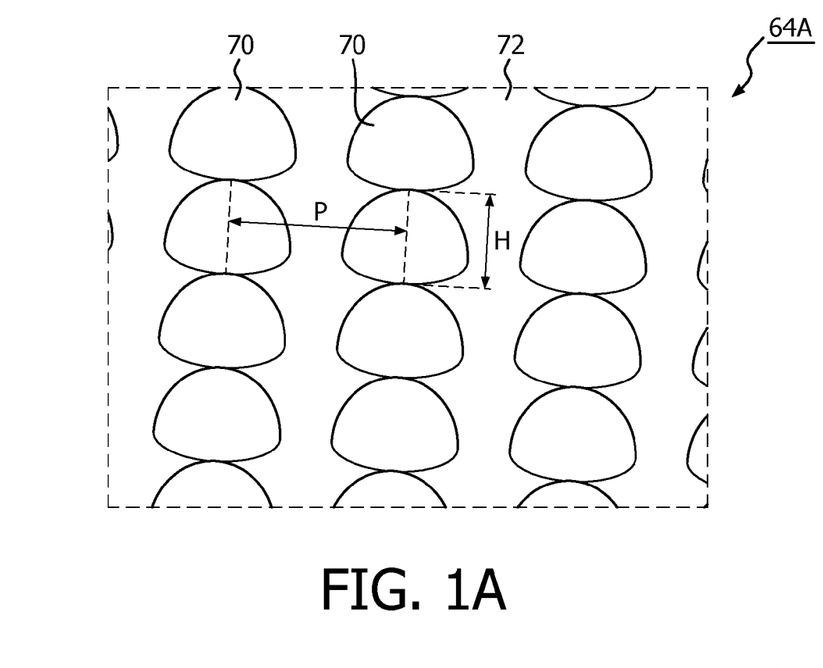
FIGS. 1A-1J are schematic isometric views of exemplary embodiments of contacting portions each having an engineered surface.
Figure 1B:
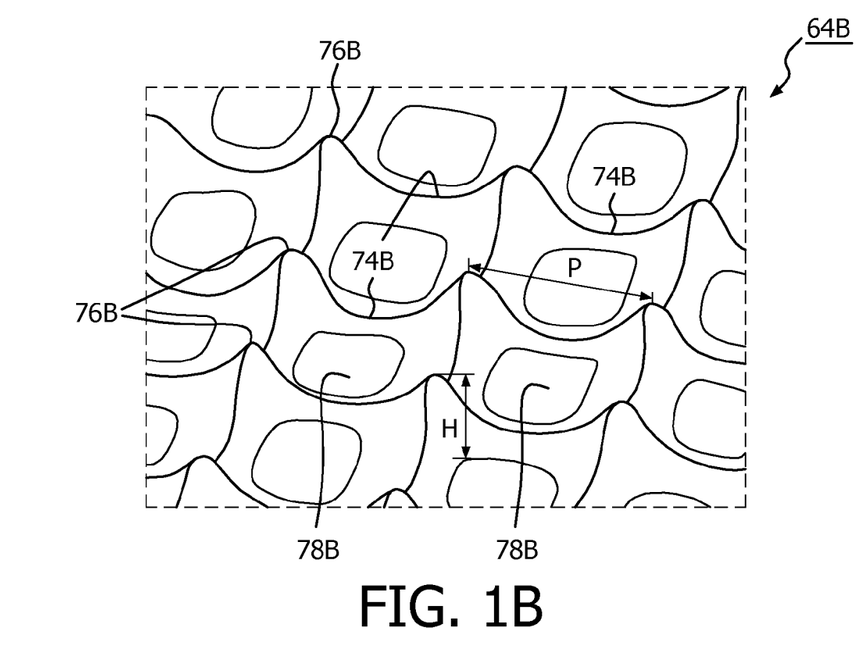
Figure 1C:
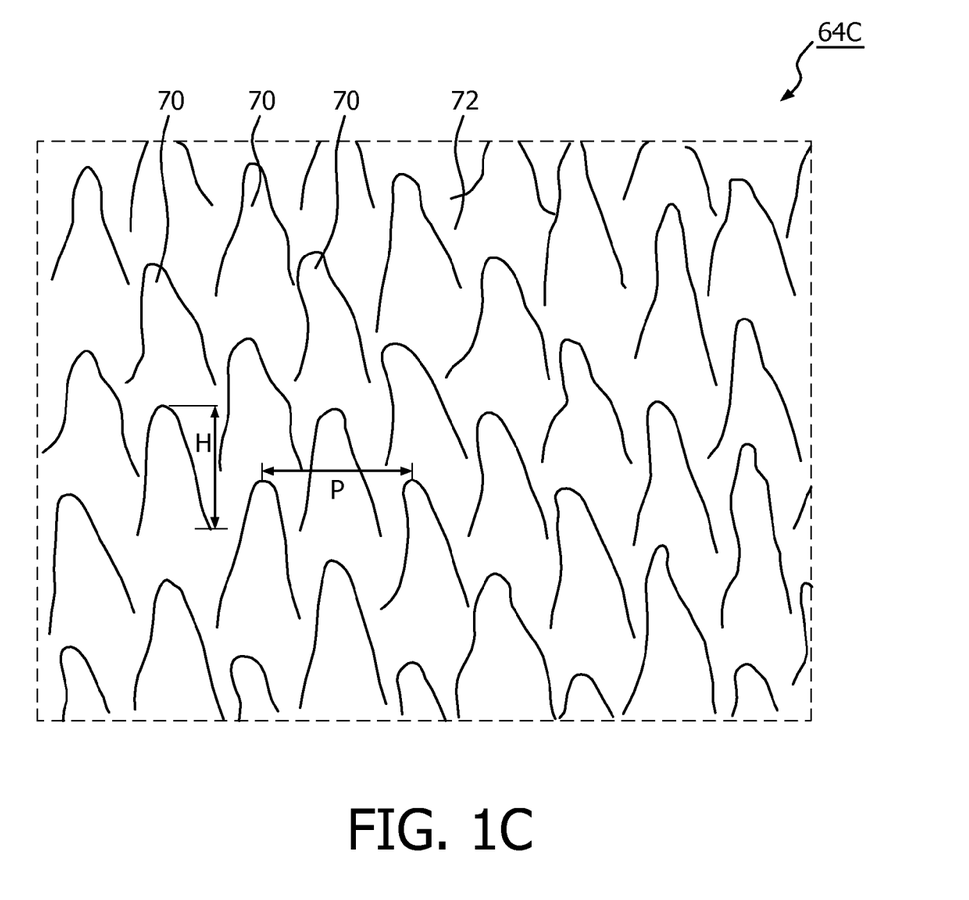

As seen in FIG. 1A, the engineered surface of contacting portion 64A includes a number of surface features 70, wherein each surface feature 70 is a dome-shaped structure extending upwardly from a bottom surface 72 of contacting portion 64A. As seen in FIG. 1B, the engineered surface of contacting portion 64B comprises a serrated configuration wherein the surface features include a number of ridges 74B and a number of pillar members 76B formed by the intersection of four adjacent ridges 74B. In addition, as seen in FIG. 1B, a valley 78B is formed in the area defined by each group of four immediately adjacent ridges 74B. As seen in FIG. 1C, the engineered surface of contacting portion 64C includes a number of surface features 70 wherein each surface feature 70 is a pillar structure extending upwardly from a bottom surface 72 of contacting portion 4C. Still further exemplary contacting portions 64G-64J comprising further exemplary engineered surfaces are shown in FIGS. 1G-1J.

Furthermore, in one exemplary embodiment of the present invention, the engineered surface of contacting portion is characterized by two particular design parameters, namely the pitch (P) of the surface features and the height (H) of the surface features. As used herein, the term "pitch" shall mean the distance between corresponding portions of immediately adjacent pairs of like surface features, and the term "height" shall mean the vertical distance between the highest point of a surface feature and the lowest surface 72 of contacting portion 64 on which the surface features sits. Referring to FIG. 1A, the pitch (P) and the height (H) of the dome-shaped surface features 70 of that embodiment are labeled P and H, respectively. Referring to FIG. 1B, in the serrated configuration of those embodiments, pitch is measured between immediately adjacent pillar members 76B and height is measured from the top of each pillar member 76B (which are the tallest surface features) to the deepest point of the valleys 78B. Alternatively, pitch may be measured between the centers of immediately adjacent ridges 74B.

In one exemplary, non limiting embodiment, the specific material may be silicone having a durometer of 40 Shore A. In another exemplary, non limiting embodiment, the specific material may be liquid silicone rubber having a durometer of 5 Shore A. Furthermore, through testing and modeling (e.g., FEM modeling using numerical simulations) of the various embodiments of contacting portion 64 described herein (with the criteria being low friction and skin comfort), the present inventors have determined that the performance of contacting portion 64 may be optimized by employing an engineered surface wherein the pitch between each immediately adjacent pair of like surface features is less than or equal to some predetermined maximum pitch value ($P_{max}$) and the height of each like surface feature is less than or equal to some predetermined height value ($H_{max}$).

Figure 2:
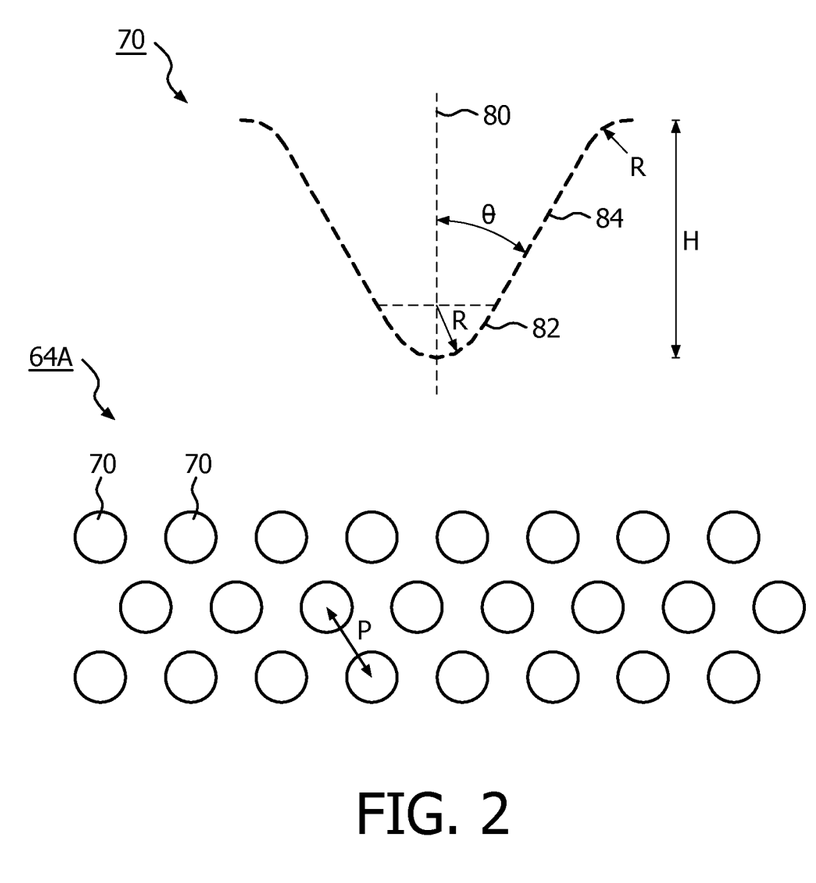
FIG. 2 is a schematic representation of the contacting portion of FIG. 1A according to one particular exemplary embodiment.

In one particular embodiment, the engineered surface is characterized by a pitch wherein the pitch is consistent and equal throughout the surface (as used herein, when comparing the pitch values of adjacent surface features within an engineered surface, "equal" shall mean the pitch values are all within a 10% or less manufacturing tolerance of one another) and is less than or equal to $P_{max}$. Examples of such surfaces wherein the pitch is consistent and equal are shown in FIGS. 1A, 1B and FIG. 2 (described below).

Figure 1D:
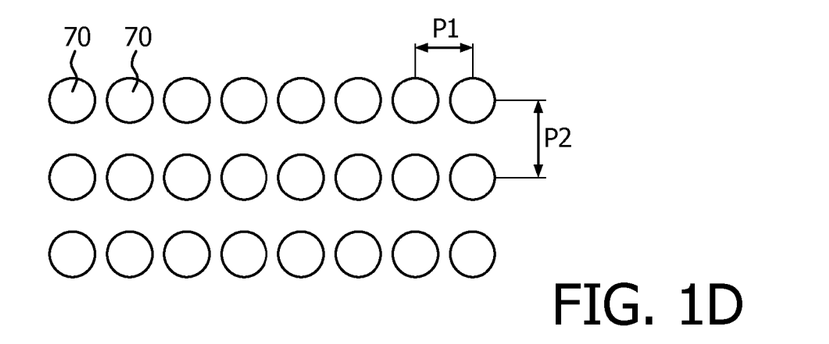
Figure 1E:
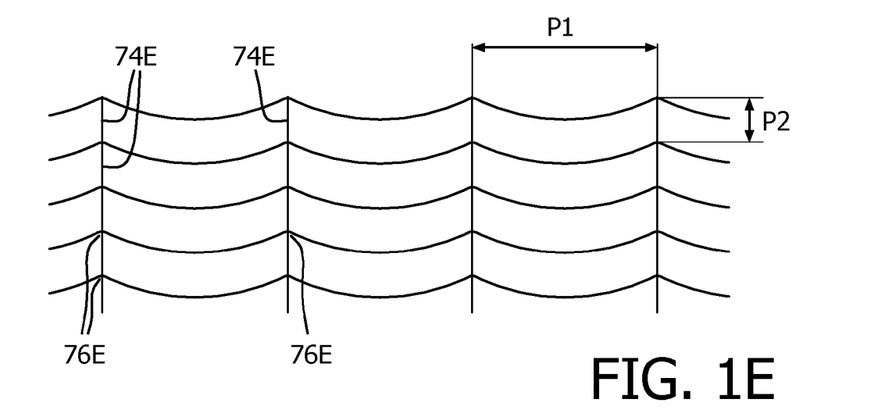

In an alternative particular embodiment, the engineered surface is characterized by a pitch wherein the pitch is anisotropic, meaning it has different dimensions/properties along different directions. More particularly, in this embodiment, the pitch will have a consistent and equal first pitch value P1 in a first direction and a consistent and equal second pitch value P2 in second direction transverse to (e.g., perpendicular to) the first direction. One example of such an embodiment is shown in FIG. 1D using dome-shaped surface features 70. Another example of such an embodiment is shown in FIG. 1E, wherein a serrated configuration as described elsewhere herein is employed.

Figure 1F:
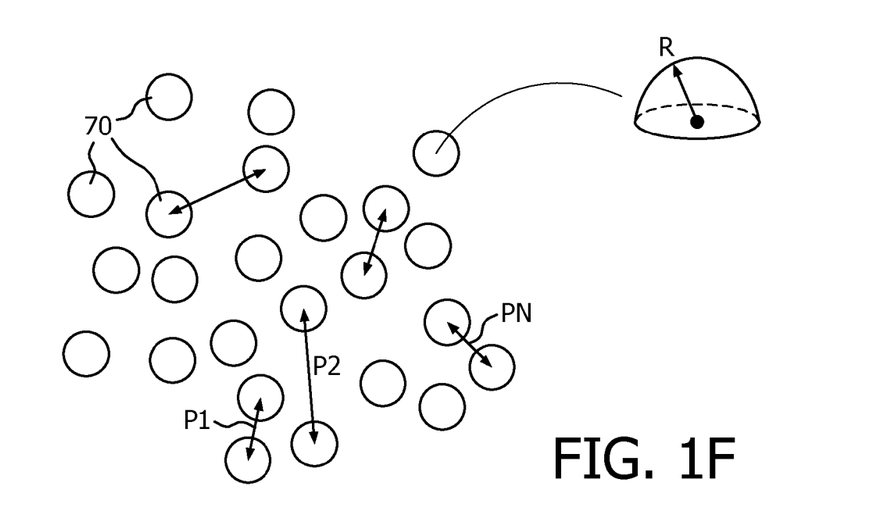
Figure 1G:
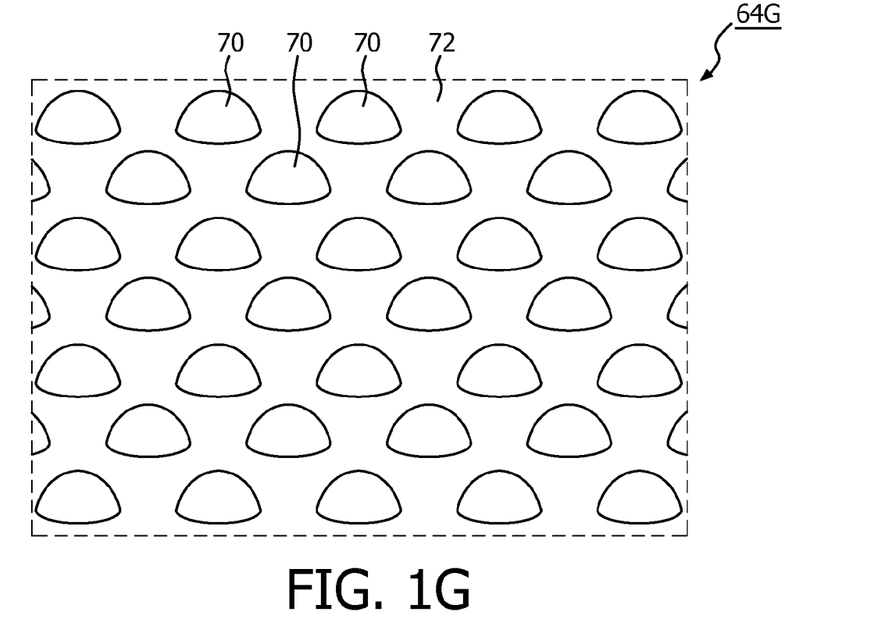
Figure 1H:
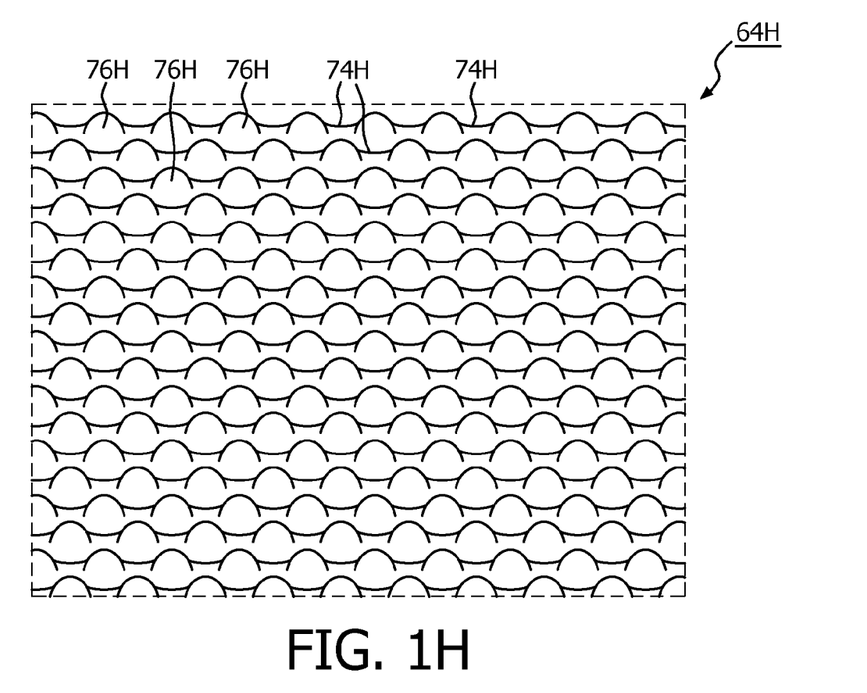
Figure 1I:
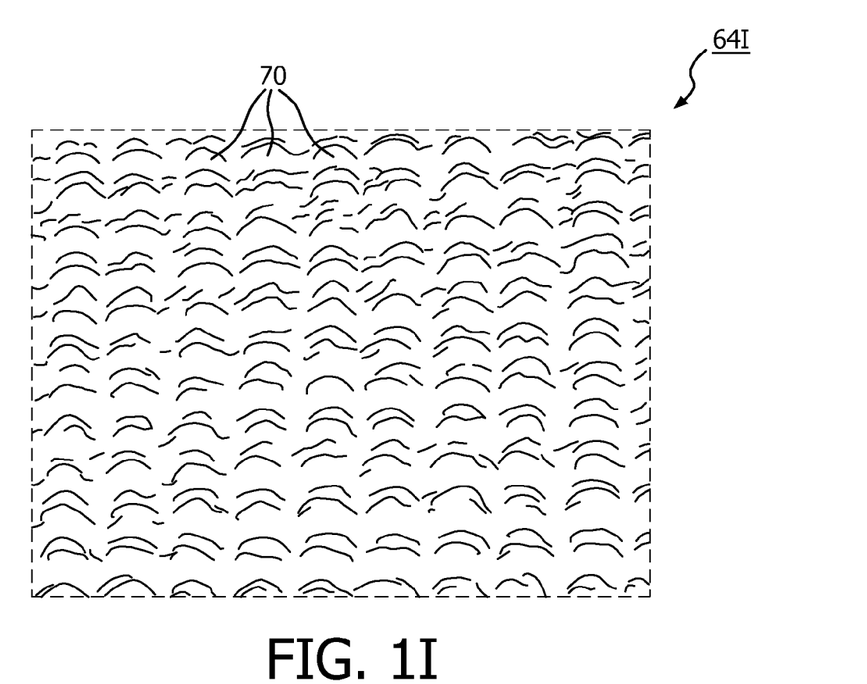
Figure 1J:
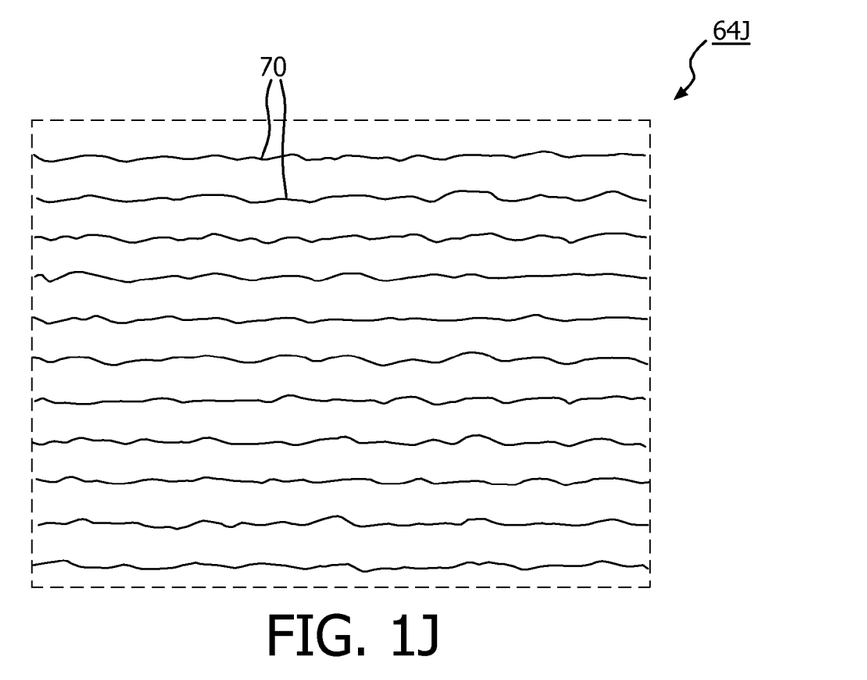

In another alternative particular embodiment, the engineered surface is characterized by a pitch wherein the pitch may vary throughout the surface but in each case is less than or equal to $P_{max}$. An example of such an embodiment is shown in FIG. 1F using dome-shaped surface features 70 (although features having other shapes may also be employed). In the illustrated embodiment, Pi=P1, P2, . . . PN, wherein $0 < Pi \leq P_{max}$, or $2R < Pi \leq P_{max}$, where R is the radius of the hemispherically-shaped dome. In one particular embodiment, each of the pitch values is within 50% of one another. In another particular embodiment, the maximum variation of the pitch values is somewhere between 10% and 50% of one another (to avoid optical stitching and vibration noise effects).

Similarly, in another particular embodiment, the engineered surface is characterized by a height wherein the height is consistent and equal throughout the surface (i.e., for each similar surface feature; as used herein, when comparing the height values of the surface features within an engineered surface, "equal" shall mean within a 30% or less manufacturing tolerance of one another) and is less than or equal to H.

Moreover, in one particular, non limiting exemplary embodiment, $P_{max}$ is equal to 100 microns and $H_{max}$ is equal to 100 microns. In other words, in this exemplary embodiment, pitch P and height H are characterized as follows: P≤100 microns and H≤100 microns. In another particular, non limiting exemplary embodiment which is a refinement of the embodiment just described, pitch P and height H are characterized as follows: P≤50 microns (or, alternatively P≤100 microns, or 20 microns≤P≤50 microns) and 10 microns≤H≤40 microns. In still a further particular, non limiting exemplary embodiment which is also a further refinement of the embodiment just described, pitch P and height H are characterized as follows: 20 microns≤P≤50 microns (or, alternatively 10 microns≤P≤50 microns, P≤50 microns, or P≤100 microns) and 10 microns≤H≤20 microns. In still a further non-limiting, exemplary embodiment, $P_{max}$ is greater than or equal to 10 microns and less than or equal to 100 microns and $H_{max}$ is greater than or equal to 10 microns and less than or equal to 100 micron. These exemplary embodiments may be implemented in, for example, any of the engineered surface configurations shown in FIGS. 1A-1C and described elsewhere herein. Through testing and modeling, the present inventors have determined that an engineered surface according to these exemplary embodiments, when implemented on a skin contacting surface such as contacting portion 64, will not have a negative effect on the user's skin during use and thus will optimize performance. For example, it has been determined that such configurations will not provide an undue stress concentration on the deeper layers of the user's skin.

Thus, based on the above, the following exemplary, non-limiting combinations of pitch and height in an engineered surface are possible:

TABLE 1

| Pitch | Height |
|---|---|
| $P_{max}$ = 100 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| $P_{max}$ = 100 microns | the height of each of the surface features is (i) ≥10 microns and ≤40 microns, or (ii) ≥10 microns and ≤20 microns |
| $P_{max}$ = 50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| $P_{max}$ = 50 microns | the height of each of the surface features is (i) ≥10 microns and ≤40 microns, or (ii) ≥10 microns and ≤20 microns |
| 10 microns ≤ $P_{max}$ ≤ 100 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| 10 microns ≤ $P_{max}$ ≤ 100 microns | the height of each of the surface features is (i) ≥10 microns and ≤40 microns, or (ii) ≥10 microns and ≤20 microns |
| the pitch between each immediately adjacent pair of the surface features is ≥10 microns and ≤50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| the pitch between each immediately adjacent pair of the surface features is ≥10 microns and ≤50 microns | the height of each of the surface features is (i) ≥10 microns and ≤40 microns, or (ii) ≥10 microns and ≤20 microns |
| the pitch between each immediately adjacent pair of the surface features is ≥20 microns and ≤50 microns | (i) $H_{max}$ = 100 microns, or (ii) $H_{max}$ = 40 microns, or (iii) $H_{max}$ = 20 microns, or (iv) $H_{max}$ ≥ 10 microns and ≤100 microns |
| the pitch between each immediately adjacent pair of the surface features is ≥20 microns and ≤50 microns | the height of each of the surface features is (i) ≥10 microns and ≤40 microns, or (ii) ≥10 microns and ≤20 microns |
| the pitch between each immediately adjacent pair of the surface features is <100 microns | the height of each of the surface features is <20 microns |
| the pitch between each immediately adjacent pair of the surface features is <30 microns (e.g., ≥10 microns and ≤25 microns) | the height of each of the surface features is <20 microns |
| the pitch between each immediately adjacent pair of the surface features is <100 microns | the height of each of the surface features is ≤15 microns |
| the pitch between each immediately adjacent pair of the surface features is <30 microns (e.g., ≥10 microns and ≤25 microns) | the height of each of the surface features is ≤15 microns |
| the pitch between each immediately adjacent pair of the surface features is <100 microns | the height of each of the surface features is ≤10 microns |
| the pitch between each immediately adjacent pair of the surface features is <30 microns (e.g., ≥10 microns and ≤25 microns) | the height of each of the surface features is ≤100 microns |

As can be seen above, in each of the described embodiments, a maximum height H is specified. One reason that a maximum height H is specified is to limit the possibility that undue deflection/deformation of the tallest surface features (e.g., dome-shaped features 70 (FIG. 1A) and pillars 76 and 70 (FIGS. 1B and 1C)) will occur when contacting surface 64 engages and applies a force to the skin of the user. Too much deflection of the tallest surface features will result in additional static friction during use, and thus is not desirable. Through testing and modeling, the present inventors have determined that a deflection of 1 micron or less in response to a normal pressure of 4.4 kPa and a friction coefficient of 1 is desired in order to avoid undesirable static friction. Thus, in one exemplary embodiment, depending on the particular material that is chosen, the maximum height is specified so as to result in surface features that are stiff/rigid enough to have a deflection of 1 micron or less. For example, with such a deflection, the height of each of the surface features may be less than 20 microns, less than or equal to 15 microns, or less than or equal to 10 microns, each with a pitch (e.g., isotropic or anisotropic) of less than 50 microns (or, alternatively a pitch (isotropic or anisotropic) of less than 30 microns). In one particular example, an engineered surface (having anisotropic pitch) was created using a nanosecond laser wherein the surface features have a pitch of 50 microns and a height of 13 microns in a first direction and a pitch of 50 microns and a height of 5 microns in a second direction.

Furthermore, the present inventors have determined that it is beneficial for the engineered surface of contacting portion 64 to prevent excessive "doming" of the user's skin (i.e., deformation of the skin toward the contacting surface 64 when it engages and applies a force to the skin) to an extent where the skin would touch the portions of the contacting surface 64 between the tallest surface features (e.g., bottom surface 72 (FIGS. 1A and 1C) and valleys 78B (FIG. 1B)). Such excessive doming is undesirable because it results in additional skin contact area and thus additional friction and potential red mark formation. Thus, in one exemplary embodiment, it is advantageous to specify a minimum height for the tallest surface features (e.g., dome-shaped features 70 (FIG. 1A) and pillars 76 and 70 (FIGS. 1B and 1C)). Once such embodiment was specified above, wherein, pitch P and height H are characterized as follows: 20 microns≤P≤50 microns and 10 microns≤H≤20 microns.

FIG. 2 is a schematic representation of one particular, non-limiting embodiment of a contacting portion having an engineered surface employing the dome-shaped features 70. In this particular embodiment, each dome-shaped feature 70 has an axi-symmetric profile as shown in FIG. 2 such that the dome-shaped feature 70 is symmetrical about a central axis 80 of the dome-shaped feature 70. In addition, each dome-shaped feature 70 includes a hemispherically-shaped tip portion 82 having a radius R that is connected to a frusto-conically-shaped bottom portion 84 (i.e., bottom portion 84 has the shape of a frustum, which as used herein shall mean a cone whose tip has been truncated by a plane parallel to its base) having a half top angle Θ measured with respect to central axis 80. In one particular, exemplary embodiment, tip portion 82 has a radius R that is between 5 and 10 microns. In another particular, exemplary embodiment, which may be combined with the previous embodiment, bottom portion 84 has a half top angle Θ that is equal to 10-60 degrees depending on the material durometer (in one specific implementation it is equal to 30 degrees for a material durometer of 40 Shore A). Furthermore, in still another particular, exemplary embodiment, in addition to the radius R and half top angle Θ parameters just specified, the pitch P and height H of exemplary contacting portion 64 shown in FIG. 2 are characterized as follows: 20 microns≤P≤50 microns and 10 microns≤H≤20 microns.

Moreover, in the exemplary embodiment, contacting portion 64 having an engineered surface as described herein is formed using a molding process, wherein the mold is formed so as to impart the engineered surface onto the molded product. For example, and without limitation, a suitable mold may be constructed by forming the mold surfaces using a laser technology (e.g., a femto-laser, a pico-laser or a nano-laser). Once the mold is formed, the laser engineered mold surface is transferred to the surface, thus giving the surface its texture. It will be understood, however, that other suitable technologies may also be employed to create a suitable mold, such as, without limitation, milling, polishing, sand blasting, etching or electric discharge machining.

As described elsewhere herein, an engineered surface that contact the user's skin may be made of a soft, flexible, cushiony, elastomeric material, such as, without limitation, silicone, an appropriately soft thermoplastic elastomer (such as thermoplastic polyurethanes (TPU)), latex, polybutadiene, a closed cell foam, or any combination of such materials. In addition, such materials may be any rubbery or elastomeric polymer material, e.g., one wherein an organic monomer is selected from the group consisting of butadiene, isoprene, dialkylsiloxanes, diarylsiloxanes, acrylic acid alkyl esters, acrylonitrile, chloroprene, fluorinated ethylene, mixtures of ethylene and vinyl acetate, mixtures of ethylene and one or more acrylic acid esters, and mixtures of ethylene with propylene and a diene. It should be noted that the above listed materials are compatible with the skin. While this is preferred, it is not mandatory and other materials that may not be optimally skin compatible may also be used.

Furthermore, in one or more particular embodiments, any of the materials listed above with the following softness and/or elasticity characteristics may be used to make the elements including an engineered surface described herein: durometer of 2-55 Shore A and elastic modulus of 0.1-3.5 MPa (or 0.1-1.5 MPa), or, alternatively, durometer of 2-50 Shore A and elastic modulus of 0.1-3.5 MPa (or 0.1-1.5 MPa), or, still alternatively, durometer of 5-50 Shore A and elastic modulus of 0.1-3.5 MPa (or 0.1-1.5 MPa). In particular examples, the following specific materials are possible: (i) silicone having durometer of 2 Shore A and an elastic modulus of 0.15 MPa, (ii) silicone having durometer of 5 Shore A and an elastic modulus of 0.3 MPa, and (iii) silicone having durometer of 40 Shore A and an elastic modulus of 1.4 MPa.

As noted elsewhere herein, one benefit of employing an engineered surface is that it provides for a certain degree of self cleaning. In particular, it has been determined that, after rubbing against the skin of the user during use, the engineered surfaces as described herein hold less skin cells than a prior art flat reference surface. Because skin organic material that adheres to a skin-contacting surface is a source of bacterial growth, and because such bacterial growth can stimulate skin redness, a configuration that can reduce the number of adhering skin cells will be advantageous.

Figure 3:
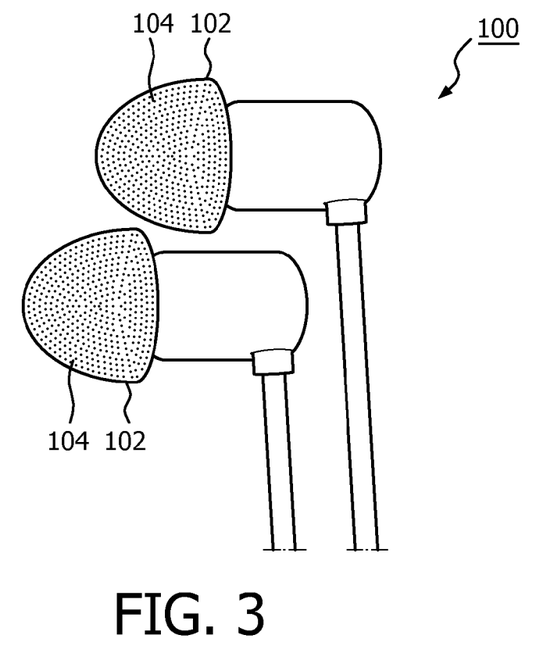
FIGS. 3 and 4 are schematic diagrams of two different embodiments of a set of earphones that each include a contacting portion having an engineered surface as described herein.
Figure 4:
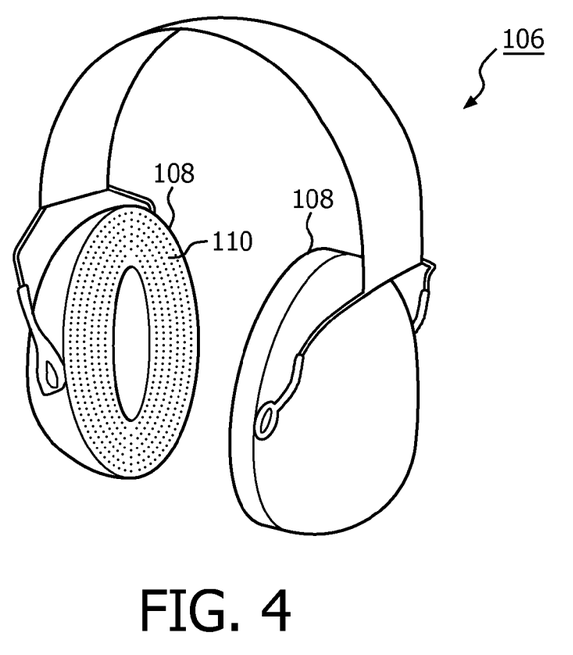
Figure 5:
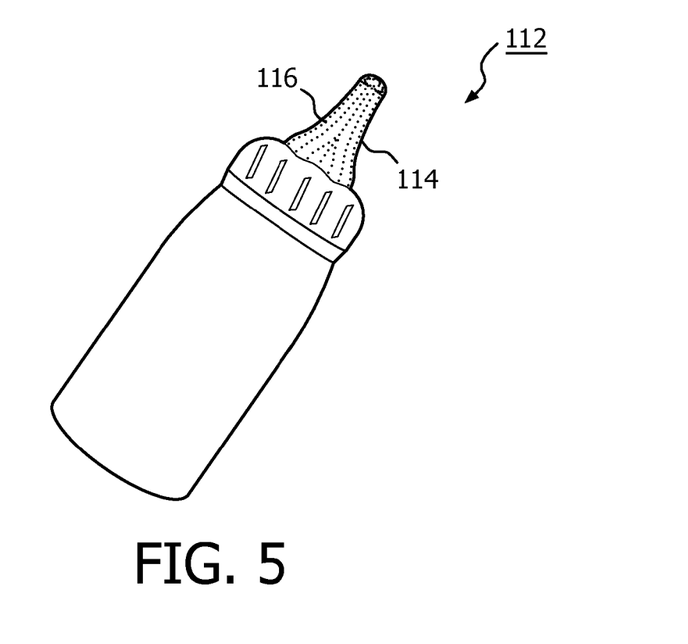
FIG. 5 is a schematic diagram of a baby bottle having a teat that includes a contacting portion having an engineered surface as described herein.
Figure 6:
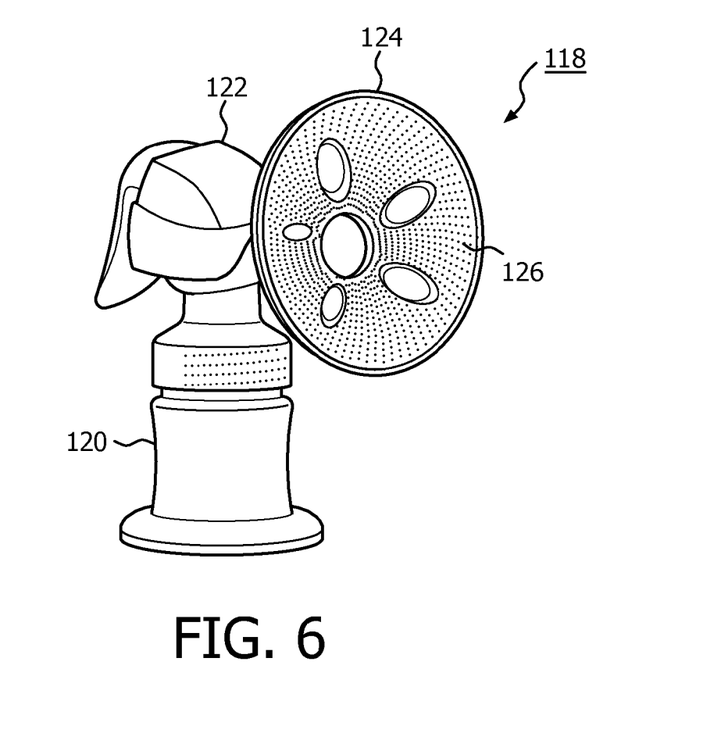
FIG. 6 is a schematic diagram of a breast pump having a breast flange that includes a contacting portion having an engineered surface as described herein.
Figure 7:
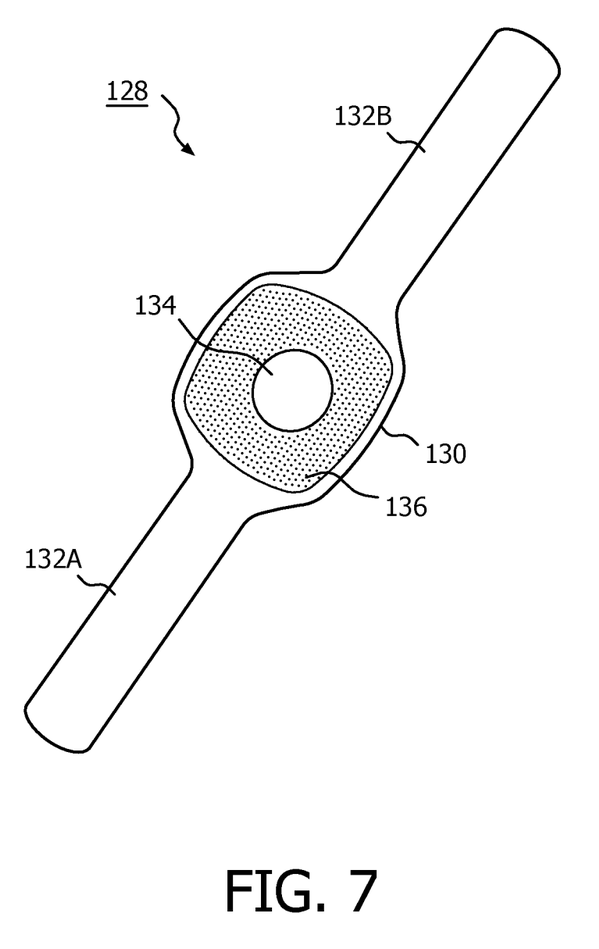
FIG. 7 is a schematic diagram of a wrist watch having heart rate monitoring functionality that includes a contacting portion having an engineered surface as described herein.

It is to be understood that an engineered surface as described herein may, for example, form part of an in-lay or patch (e.g., disposable) Engineered surfaces as described herein may be used on contacting portions of different types of devices, such as, without limitation, It is also to be understood that the use of the engineered surfaces as described herein are not limited to any specific device. Instead, the engineered surfaces can be used to form tissue contacting portions on a wide variety of devices. For example, as seen in FIG. 3, which is a schematic diagram of one embodiment of a set of earphones 100 having earpieces 102 formed from a soft, flexible elastomeric material, such as, without limitation, silicone, the engineered surfaces as described herein in the various embodiments can be used to form skin contacting portions 104 on earpieces 102. Similarly, as seen in FIG. 4, which is a schematic diagram of another embodiment of a set of earphones 106 having earpieces 108 formed from a soft, flexible elastomeric material, such as, without limitation, silicone, the engineered surfaces as described herein in the various embodiments can be used to form skin contacting portions 110 on earpieces 108. As another example, as seen in FIG. 5, which is a schematic diagram of one embodiment of a baby bottle 112 having a nipple or teat 114 formed from a soft, flexible elastomeric material, such as, without limitation, silicone, the engineered surfaces as described herein in the various embodiments can be used to form a tissue contacting portion 116 on nipple or teat 114. As still another example, as seen in FIG. 6, which is a schematic diagram of one embodiment of a breast pump 118 having a receptacle 120, a handle driven pump assembly 122, and a breast flange 124 formed from a soft, flexible elastomeric material, such as, without limitation, silicone, the engineered surfaces as described herein in the various embodiments can be used to form a tissue contacting portion 126 of breast flange 124. Yet another example is shown in FIG. 7, which is a rear schematic diagram of one embodiment of a wrist watch 128 having heart rate monitoring functionality. As seen in FIG. 7, watch 128 includes a central portion 130 and straps 132A and 132B. Central portion 130 includes a sensor area 134 structured to hold a sensor and a tissue contacting portion 136 surrounding the sensor area 134. The tissue contacting portion 136 includes an engineered surface as described herein in the various embodiments. The main function of the engineered surface is to prevent slip between the sensor provided in sensor area 134 and the skin while at the same time providing skin comfort. In one exemplary embodiment, tissue contacting portion 136 comprises a silicone rubber patch attached to the back side of watch 128. In addition, the sensor application as just described is not limited to wrist watches, but instead can be any type of sensor application to the skin. It is to be understood that the contacting portions 104, 110, 116, 126, 136 can, alternatively, be provided over only a portion of the earpieces 102, the earpieces 108, the nipple or teat 114, the breast flange 124, or the watch 128 as the case may be, in a select pattern or select locations.

As described elsewhere herein, FIG. 2 is a schematic representation of one particular, non-limiting embodiment of contacting portion 64A having an engineered surface employing dome-shaped features 70 wherein each dome-shaped feature 70 has an axi-symmetric profile and is symmetrical about a central axis 80 of the dome-shaped feature 70. In addition, each dome-shaped feature 70 includes a hemispherically-shaped tip portion 82 having a radius R that is connected to a frusto-conically-shaped bottom portion 84.

Figure 8:
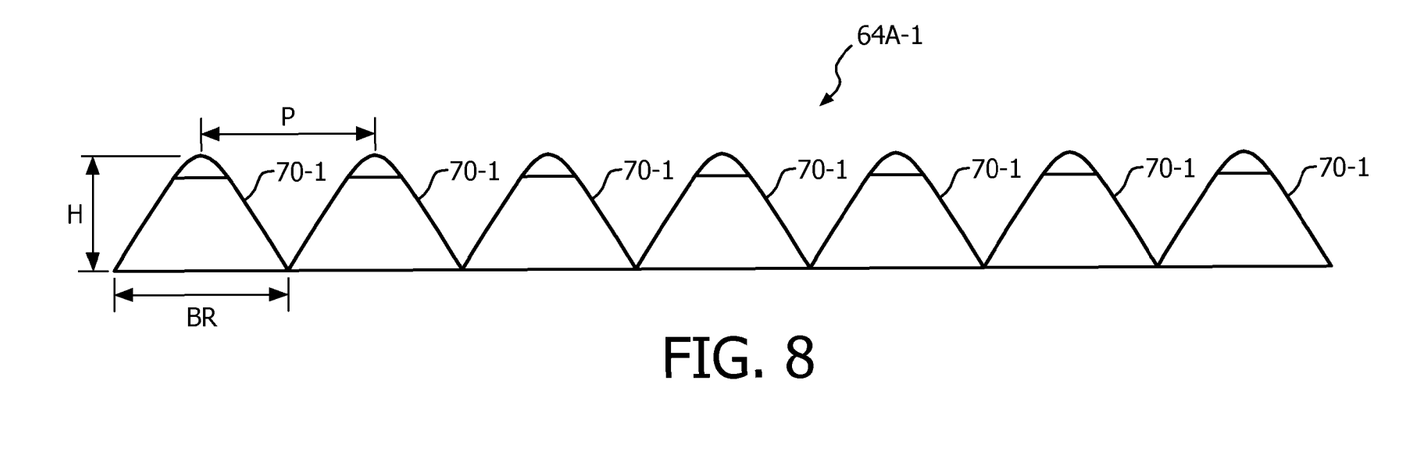
FIGS. 8-11 are cross sectional views of the contacting portion of FIG. 2 according to various particular alternative implementations.

FIG. 8 is a cross-sectional view of a specific, non-limiting implementation of contacting portion 64A of FIG. 2, labeled 64A-1. In contacting portion 64A-1, the engineered surface has the following parameters/characteristics: (i) contacting portion 64A-1 is made of a material, such as silicone, having a durometer of 5 Shore A and an elastic modulus of 0.1-1.5 MPa (e.g. 0.3 MPa), (ii) each dome-shaped feature 70-1 has a base radius (BR) equal to 7.5 microns, (iii) the pitch P of dome-shaped features 70-1 in contacting portion 64A-1 is 15 microns, (iv) the height of each dome-shaped feature 70-1 is 10 microns, and (v) the dome-shaped features 70-1 in contacting portion 64A-1 have a deflection of 1 micron or less (e.g., 0.869926 microns or less) in response to a normal pressure of 0.01 MPa and a friction coefficient of 1.

Figure 9:
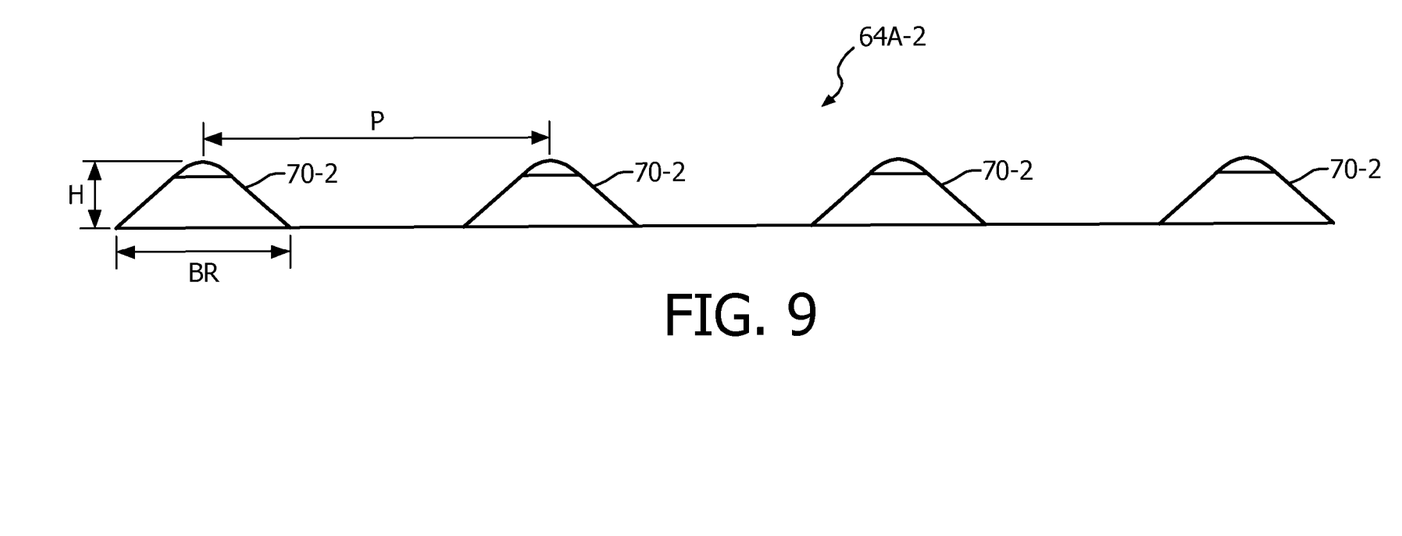

FIG. 9 is a cross-sectional view of another specific, non-limiting implementation of contacting portion 64A of FIG. 2, labeled 64A-2. In contacting portion 64A-2, the engineered surface has the following parameters/characteristics: (i) contacting portion 64A-2 is made of a material, such as silicone, having a durometer of 5 Shore A and an elastic modulus of 0.1-1.5 MPa (e.g. 0.3 MPa), (ii) each dome-shaped feature 70-2 has a base radius (BR) equal to 7.5 microns, (iii) the pitch P of dome-shaped features 70-2 in contacting portion 64A-2 is 30 microns, (iv) the height of each dome-shaped feature 70-2 is 5 microns, and (v) the dome-shaped features 70-2 in contacting portion 64A-2 have a deflection of 0.5 microns or less (e.g, 0.434963 microns or less) in response to a normal pressure of 0.01 MPa and a friction coefficient of 1.

Figure 10:
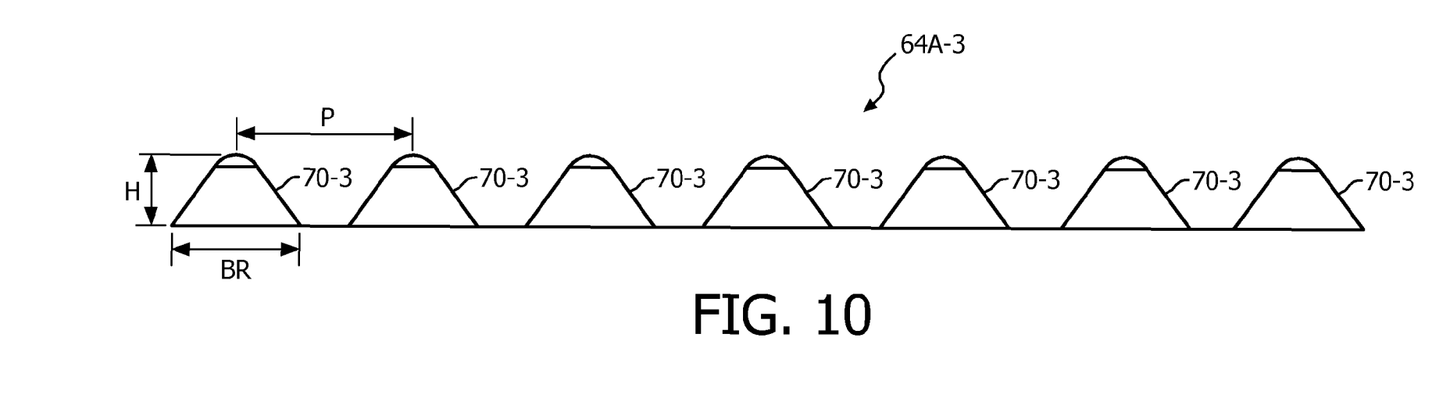

FIG. 10 is a cross-sectional view of yet another specific, non-limiting implementation of contacting portion 64A of FIG. 2, labeled 64A-3. In contacting portion 64A-3, the engineered surface has the following parameters/characteristics: (i) contacting portion 64A-3 is made of a material, such as silicone, having a durometer of 5 Shore A and an elastic modulus of 0.1-1.5 MPa (e.g. 0.3 MPa), (ii) each dome-shaped feature 70-3 has a base radius (BR) equal to 5 microns, (iii) the pitch P of dome-shaped features 70-3 in contacting portion 64A-3 is 15 microns, (iv) the height of each dome-shaped feature 70-3 is 5 microns, and (v) the dome-shaped features 70-3 in contacting portion 64A-3 have a deflection of 0.6 microns or less (e.g., 0.5505 microns or less) in response to a normal pressure of 0.01 MPa and a friction coefficient of 1.

Figure 11:
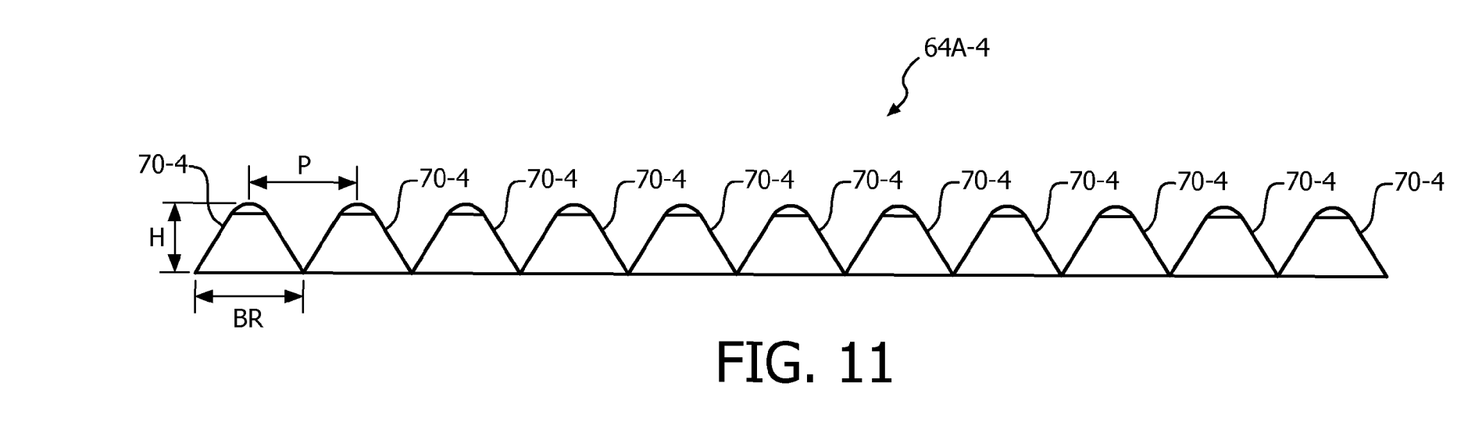

FIG. 11 is a cross-sectional view of still another specific, non-limiting implementation of contacting portion 64A of FIG. 2, labeled 64A-4. In contacting portion 64A-4, the engineered surface has the following parameters/characteristics: (i) contacting portion 64A-4 is made of a material, such as silicone, having a durometer of 5 Shore A and an elastic modulus of 0.1-1.5 MPa (e.g. 0.3 MPa), (ii) each dome-shaped feature 70-4 has a base radius (BR) equal to 5 microns, (iii) the pitch P of dome-shaped features 70-4 in contacting portion 64A-4 is 10 microns, (iv) the height of each dome-shaped feature 70-4 is 5 microns, and (v) the dome-shaped features 70-4 in contacting portion 64A-4 have a deflection of 0.3 microns or less (e.g., 0.244667 microns or less) in response to a normal pressure of 0.01 MPa and a friction coefficient of 1.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An apparatus structured to contact only the external surface of external tissue of a user during use thereof and not be inserted into or through the external tissue of the user, comprising:
   a contacting portion structured to directly engage the external tissue, wherein at least a section of the contacting portion has an engineered surface comprising a plurality of non-random, predesigned surface features each having a like geometry, wherein in the section a pitch between each immediately adjacent pair of the surface features is less than or equal to a predetermined maximum pitch value, the pitch being defined as the distance between a peak of a first surface feature and a peak of a second surface feature immediately adjacent the first surface feature, and wherein in section a height of each of the surface features is less than or equal to a predetermined maximum height value, said predetermined maximum pitch value being 100 microns, said predetermined maximum height value being 100 microns,
   wherein at least one of:
   the engineered surface comprises a plurality of second surface features, each of the second surface features being a ridge member, each of the surface features being a pillar member formed by an intersection of four adjacent ones of the ridges, and
   the engineered surface is engineered to prevent slip between the engineered surface and the external tissue of the user and each of the surface features is dome-shaped and has a tip portion coupled to a base portion, wherein the tip portion has a radius of between 5 and 10 microns, and wherein the base portion has a half top angle measured with respect to a central axis of the surface feature equal to or between 10 and 60 degrees.

2. The apparatus according to claim 1, wherein the contacting portion is made of a material having a durometer of 5 Shore A and an elastic modulus of 0.1-1.5 MPa.

3. An apparatus structured to contact only the external surface of external tissue of a user during use thereof and not be inserted into or through the external tissue of the user, comprising:
a contacting portion structured to directly engage the external tissue, wherein at least a section of the contacting portion has an engineered surface comprising a plurality of non-random, predesigned surface features each having a like geometry, wherein in the section a pitch between each immediately adjacent pair of the surface features is less than or equal to a predetermined maximum pitch value, the pitch being defined as the distance between a peak of a first surface feature and a peak of a second surface feature immediately adjacent the first surface feature, and wherein in section a height of each of the surface features is less than or equal to a predetermined maximum height value, said predetermined maximum pitch value being 100 microns, said predetermined maximum height value being 100 microns,
wherein the apparatus is selected from the group consisting of: (i) a breast pump, wherein the contacting portion is part of a breast flange, (ii) a set of earphones, wherein the contacting portion is part of an earpiece, (iii) a baby bottle, wherein the contacting portion is part of a teat, and (iv) a sensor device, wherein the contacting portion is provided on a skin contacting surface of the sensor device; and
wherein at least one of:
the engineered surface comprises a plurality of second surface features, each of the second surface features being a ridge member, each of the surface features being a pillar member formed by an intersection of four adjacent ones of the ridges, and
the pitch between each immediately adjacent pair of the surface features is 10-30 microns, each of the surface features has a base portion having a radius of 5-7.5 microns, the height of each of the surface features is less than or equal to 10 microns, and a deflection of each of the surface features is equal to 1 micron or less in response to a normal pressure of 0.01 MPa.

4. The apparatus according to claim 3, wherein in the section the height of each of the surface features is equal to one another.

5. The apparatus according to claim 3, wherein the pitch between each immediately adjacent pair of the surface features is equal, or wherein the engineered surface demonstrates either: (i) anisotropic pitch such that the pitch between each immediately adjacent pair of the surface features in a first direction is equal to a first pitch value and the pitch between each immediately adjacent pair of the surface features in a second direction transverse to the first direction is equal to a second pitch value different than the first pitch value, or (ii) variable pitch such that the pitch between each immediately adjacent pair of the surface features varies but in each cases is less than or equal to the predetermined maximum pitch value.

6. An apparatus structured to contact only the external surface of external tissue of a user during use thereof and not be inserted into or through the external tissue of the user, comprising:
a contacting portion structured to directly engage the external tissue, wherein at least a section of the contacting portion has an engineered surface comprising a plurality of non-random, predesigned surface features each having a like geometry, wherein in the section a pitch between each immediately adjacent pair of the surface features is less than or equal to a predetermined maximum pitch value, the pitch being defined as the distance between a peak of a first surface feature and a peak of a second surface feature immediately adjacent the first surface feature, and wherein in section a height of each of the surface features is less than or equal to a predetermined maximum height value, said predetermined maximum pitch value being 100 microns, said predetermined maximum height value being 100 microns, the contacting portion being made of an elastomeric material having a durometer of 2-55 Shore A, an elastic modulus of 0.01-1.5 MPa, a height of 5-20 microns, a deflection of 1 micron or less in response to a pressure of 0.01 MPa, a base radius of 5-10 microns, and a pitch of 10-30 microns; and
wherein at least one of:
the engineered surface is engineered to prevent slip between the engineered surface and the external tissue of the user and each of the surface features is dome-shaped and has a tip portion coupled to a base portion, wherein the tip portion has a radius of between 5 and 10 microns, and wherein the base portion has a half top angle measured with respect to a central axis of the surface feature equal to or between 10 and 60 degrees, and
each of the surface features has a base portion having a radius of 5-7.5 microns, and the height of each of the surface features is less than or equal to 10 microns.

7. An apparatus structured to contact an external surface of skin of a user during use thereof comprising:
a contacting portion structured to directly engage the skin wherein at least a section of the contacting portion has an engineered surface configured to prevent slip between the contacting portion and the skin, the engineered surface comprising a plurality of non-random, predesigned surface features each having a like geometry, wherein a pitch defined as the distance between a peak of a first surface feature and a peak of a second surface feature immediately adjacent the first surface feature between each immediately adjacent pair of the surface features is less than or equal to 100 microns, and wherein a height of each of the surface features is less than or equal to 100 microns, wherein the engineered surface includes silicone with a durometer of 2-50 Shore A and an elastic modulus of 0.1 to 3.5 MPa, the silicone material defining dome-shaped surface features with a maximum pitch of 50 microns, a maximum height of 40 microns, and a tip portion radius between 5-10 microns; and
wherein at least one of:
the engineered surface comprises a plurality of second surface features, each of the second surface features being a ridge member, each of the surface features being a pillar member formed by an intersection of four adjacent ones of the ridges,
each of the surface features has a tip portion coupled to a base portion, wherein the base portion has a half top angle measured with respect to a central axis of the surface feature equal to or between 10 and 60 degrees, and the pitch between each immediately adjacent pair of the surface features is 10-30 microns, each of the surface features has a base portion having a radius of 5-7.5 microns, the height of each of the surface features is less than or equal to 10 microns, and a deflection of each of the surface features is equal to 1 micron or less in response to a normal pressure of 0.01 MPa.

8. The apparatus according to claim 7, wherein the durometer is 5 Shore A and the elastic modulus is 0.3 MPa.

9. The apparatus according to claim 7, wherein the pitch is between 10 and 50 microns and the height is between 10 and 40 microns.

10. The apparatus according to claim 9, wherein each of the surface features has a tip portion coupled to a base portion, wherein the base portion has a half top angle measured with respect to a central axis of the surface feature equal to between 10 and 60 degrees, such that excessive doming of the user's skin is prevented.

11. An apparatus selected from the group consisting of: (i) a breast pump with a contacting portion on a part of a breast flange, (ii) a set of earphones with a contacting portion on a part of an earpiece, (iii) a baby bottle with a contacting portion on a part of a teat, and (iv) a sensor device with a contacting portion on a skin contacting surface of the sensor device, wherein the contacting portion has an engineered surface configured to prevent slip between the apparatus and skin of a user, the engineered surface comprising:

a soft molded silicone material having a durometer of 2-50 Shore A, the silicone material defining dome-shaped surface features with a maximum pitch of 50 microns, a maximum height of 40 microns, and a tip portion radius between 5-10 microns, the pitch being defined as the distance between a peak of a first surface feature and a peak of a second surface feature immediately adjacent the first surface feature.

* * * * *